(12) United States Patent
Roh et al.

(10) Patent No.: US 12,157,761 B2
(45) Date of Patent: Dec. 3, 2024

(54) LONG-ACTING EXENDIN-4 AND USE THEREOF

(71) Applicant: INDUSTRY-ACADEMIC COOPERATION FOUNDATION GYEONGSANG NATIONAL UNIVERSITY, Gyeongsangnam-do (KR)

(72) Inventors: Gu Seob Roh, Gyeongsangnam-do (KR); Meong Cheol Shin, Gyeongsangnam-do (KR); Jong Youl Lee, Gyeongsangnam-do (KR); Taehoon Park, Gyeongsangnam-do (KR)

(73) Assignee: INDUSTRY-ACADEMIC COOPERATION FOUNDATION GYEONGSANG NATIONAL UNIVERSITY, Gyeongsangnam-do (KR)

( * ) Notice: Subject to any disclaimer, the term of this patent is extended or adjusted under 35 U.S.C. 154(b) by 757 days.

(21) Appl. No.: 17/299,274

(22) PCT Filed: Nov. 27, 2019

(86) PCT No.: PCT/KR2019/016412
§ 371 (c)(1),
(2) Date: Jun. 2, 2021

(87) PCT Pub. No.: WO2020/116847
PCT Pub. Date: Jun. 11, 2020

(65) Prior Publication Data
US 2022/0025011 A1    Jan. 27, 2022

(30) Foreign Application Priority Data
Dec. 6, 2018 (KR) .......................... 10-2018-0155957

(51) Int. Cl.
| | | |
|---|---|---|
| C07K 14/605 | (2006.01) | |
| A61K 38/00 | (2006.01) | |
| A61P 1/16 | (2006.01) | |
| A61P 3/04 | (2006.01) | |
| A61P 3/10 | (2006.01) | |
| C07K 16/28 | (2006.01) | |
| C12P 21/02 | (2006.01) | |

(52) U.S. Cl.
CPC .............. *C07K 14/605* (2013.01); *A61P 1/16* (2018.01); *A61P 3/04* (2018.01); *A61P 3/10* (2018.01); *C07K 16/283* (2013.01); *C12P 21/02* (2013.01); *A61K 38/00* (2013.01); *C07K 2319/31* (2013.01)

(58) Field of Classification Search
CPC ............... C07K 14/605; C07K 16/283; C07K 2319/31; C07K 2318/20; C07K 14/57563; C07K 2318/00; C07K 2319/00; A61P 1/16; A61P 3/04; A61P 3/10; A61P 25/18; C12P 21/02; A61K 38/00; A61K 38/26; A61K 47/64; A61K 47/68; A61K 47/643; A61K 47/6811; Y02A 50/30; A23L 33/18; C12N 15/70
See application file for complete search history.

(56) References Cited

U.S. PATENT DOCUMENTS 9,382,304 B2 * 7/2016 Erickson ................ A61K 47/65
2014/0170142 A1 6/2014 Lubman et al.

FOREIGN PATENT DOCUMENTS

| JP | 2016188225 A | 11/2016 | |
|---|---|---|---|
| KR | 1020140071350 B1 | 6/2014 | |
| KR | 1020150016585 A | 2/2015 | |
| KR | 1020150064093 B1 | 6/2015 | |
| KR | 1020170037564 A | 4/2017 | |
| KR | 1020170054440 A | 5/2017 | |
| KR | 1020180071241 A | 6/2018 | |
| WO | 2011153965 A1 | 12/2011 | |
| WO | WO-2016042083 A1 * | 3/2016 | ............. A61K 38/16 |

* cited by examiner

*Primary Examiner* — Brad Duffy
*Assistant Examiner* — Amber K Faust
(74) *Attorney, Agent, or Firm* — HULTQUIST, PLLC; Steven J. Hultquist

(57) ABSTRACT

The present invention relates to a long-acting exendin-4 in which an albumin binding domain (ABD) and an anti-FcRn affibody are fused to exendin-4, and a use thereof. A long-acting exendin-4 according to the present invention has an in vivo half-life that is significantly increased over that of exendin-4, which is conventionally used as an agent for treating diabetes, and resultantly acts as a diabetes therapeutic agent, which is a conventional use of exendin-4, and also exhibits both an effect of treating other metabolic diseases and diabetes complications, such as obesity and fatty liver, and an effect of alleviating cognitive impairment caused by metabolic diseases.

6 Claims, 8 Drawing Sheets
(8 of 8 Drawing Sheet(s) Filed in Color)
Specification includes a Sequence Listing.

LONG-ACTING EXENDIN-4 AND USE THEREOF

CROSS-REFERENCE TO RELATED APPLICATIONS

This is a U.S. national phase under 35 USC § 371 of International Patent Application No. PCT/KR2019/016412 filed Nov. 27, 2019, which in turn claims priority under 35 USC § 119 of Korean Patent Application No. 10-2018-0155957 filed Dec. 6, 2018. The disclosures of all such applications are hereby incorporated herein by reference in their respective entireties, for all purposes.

REFERENCE TO SEQUENCE LISTING SUBMITTED VIA PATENT CENTER

This application includes an electronically submitted sequence listing in .txt format. The .txt file contains a sequence listing entitled "565_UpdatedSeqListing_ST25.txt" created on Jul. 12, 2024 and is 4,836 bytes in size. The sequence listing contained in this .txt file is part of the specification and is hereby incorporated by reference herein in its entirety.

TECHNICAL FIELD

The present invention relates to a long-acting exendin-4 and a use thereof, and more particularly to a long-acting exendin-4 in which an albumin-binding domain (ABD) and an anti-FcRn affibody are fused to exendin-4 and the use thereof for the treatment, alleviation and prevention of metabolic diseases such as diabetes, fatty liver, and obesity and cognitive impairment.

BACKGROUND ART

Exendin-4 is a peptide 39 amino acids in length produced by the salivary glands of Gila monsters (*Heloderma suspectum*). Exendin-4 is an activator of the glucagon-like peptide-1 (GLP-1) receptor, but does not significantly activate the glucagon receptor. Exendin-4 shares most of the blood glucose control activity observed in GLP-1. Clinical and nonclinical studies show that exendin-4 exhibits several beneficial antidiabetic properties, including promoting glucose-dependent insulin synthesis and secretion, suppressing glucose-dependent glucagon secretion, slowing gastric emptying, increasing food intake, weight loss and beta cell mass, and increasing markers having beta cell functions (Korean Patent Laid-open Publication No. 10-2015-0064093). In 2005, the synthetic exendin-4 Byetta® was developed by the pharmaceutical companies Eli Lilly and Emily and approved as a diabetic therapeutic agent. However, exendin-4 is rapidly eliminated from the kidneys due to the low molecular weight thereof, and thus is incapable of stimulating GLP-1R for a long period of time. Thus, Byetta® should be administered twice a day to achieve an effective therapeutic effect and thus has many problems associated with convenience as a therapeutic agent.

Therefore, in order to improve the therapeutic effect of type 1 diabetes and type 2 diabetes, the development of long-acting exendin-4 is required, and many pharmaceutical companies have conducted research to increase the residence time in the body in hypoglycemia by modifying the molecular structure of exendin-4. For example, WO 2011/153965 discloses fusion of the Fc region of human IgG2 to exendin-4 through a linking peptide to increase the in-vivo half-life, and Korean Patent Laid-open Publication No. 10-2018-0090750 suggests a long-acting exendin-4 to which immunoglobulin Fc is linked through polyethylene glycol to increase the in-vivo half-life.

GLP-1 receptor agonists can improve the cognitive function of rodents, and GLP-1 receptor knock-out mice have a phenotype characterized by learning deficits stored after transfer of hippocampal GLP-1 receptor genes. Recently, Isaacson et al. revealed chronic therapeutic effects of exendin-4 on hippocampal-related cognition and mood-related behaviors in adult rodents. In other research, multiple neuropathy found in the dorsal ganglia of a diabetes mouse model was reversed using exendin-4. It has been found that another GLP-1 analogue, liraglutide, exerts beneficial effects on cognitive functions and hippocampal synaptic plasticity in mice suffering from high-fat-diet-induced obesity and insulin resistance (Korean Patent Laid-open Publication 10-2014-0071350).

However, the half-life of long-acting exendin-4 as described above is still short. Therefore, there is a need to develop therapeutic agents that have a further extended half-life and are capable of alleviating all complications of the metabolic syndrome, such as alleviation of fatty liver and cognitive impairment, as well as anti-obesity and anti-diabetic effects. Accordingly, the present inventors have developed exendin-4, which has a remarkably longer plasma half-life than conventional long-acting agents, and demonstrated through animal experiments that the resultant long-acting exendin-4 can be developed as a therapeutic agent that is capable of treating both diabetes and metabolic diseases, which are complications of diabetes, such as fatty liver and obesity, and that exhibits an effect of alleviating cognitive disorders.

Disclosure

Therefore, it is one object of the present invention to provide a long-acting exendin-4 with an increased in-vivo half-life, and uses thereof for the treatment, prevention and alleviation of metabolic diseases and cognitive impairment.

In order to accomplish the object described above, the present invention provides a long-acting exendin-4 in which an albumin-binding domain (ABD) and an anti-FcRn affibody (aFaff) are fused to exendin-4.

The present invention also provides a pharmaceutical composition for treating metabolic diseases including the long-acting exendin-4 as an active ingredient.

The present invention also provides a food composition for preventing or alleviating metabolic diseases including the long-acting exendin-4 as an active ingredient.

The present invention also provides a recombinant vector including a nucleic acid encoding exendin-4, a nucleic acid encoding an albumin-binding domain (ABD), and a nucleic acid encoding an anti-FcRn affibody (aFaff).

The present invention also provides a recombinant microorganism for producing long-acting exendin-4 introduced with the recombinant vector.

The present invention also provides a pharmaceutical composition for treating cognitive impairment including the long-acting exendin-4 as an active ingredient.

The present invention also provides a food composition for improving cognitive ability including the long-acting exendin-4 as an active ingredient.

The present invention also provides a method for treating, preventing or alleviating metabolic diseases including administering the long-acting exendin-4 to a subject in need thereof.

The present invention also provides a method for treating or preventing cognitive impairment or a method for improving cognitive ability comprising administering the long-acting exendin-4 to a subject in need thereof.

The present invention also provides a method for improving cognitive ability including administering the long-acting exendin-4 to a subject in need thereof.

The present invention also provides the use of the long-acting exendin-4 for the treatment, prevention, or alleviation of metabolic diseases.

The present invention also provides the use of the long-acting exendin-4 for the treatment or prevention of cognitive impairment and improvement of cognitive ability.

The present invention also provides the use of long-acting exendin-4 for the preparation of a drug for treating, preventing or ameliorating metabolic diseases.

The present invention also provides the use of long-acting exendin-4 for the preparation of a drug for treating or preventing cognitive impairment or for improving cognitive ability.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
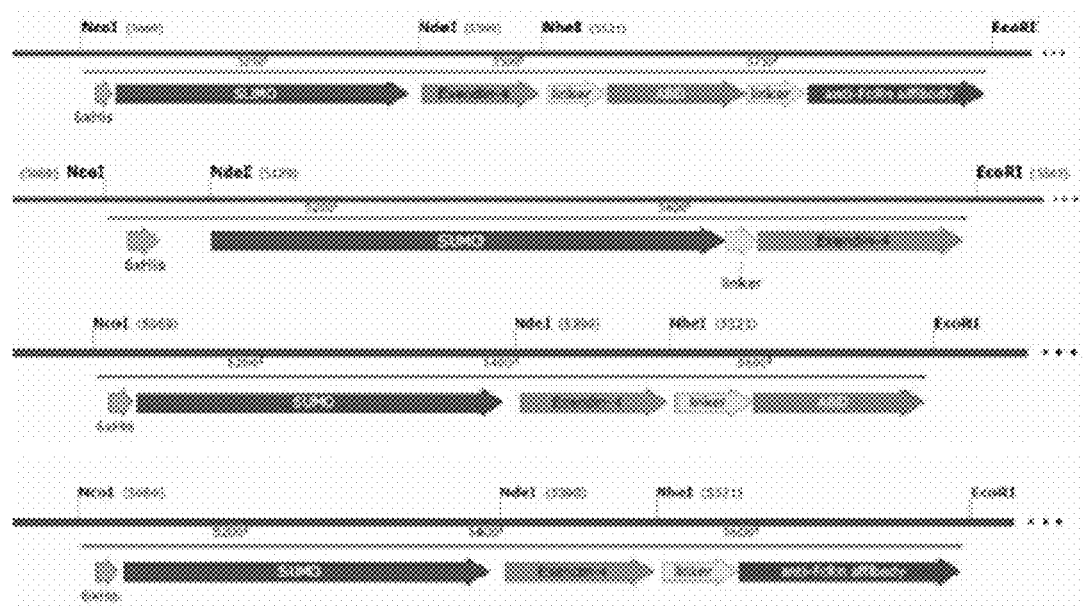
FIG. 1 is a schematic diagram illustrating a portion inserted into the pET28a plasmid for the expression of exendin-4-ABD-aFaff, exendin-4, exendin-4-aFaff and exendin-ABD.

Unless defined otherwise, all technical and scientific terms used herein have the same meanings as those appreciated by those skilled in the field to which the present invention pertains. In general, the nomenclature used herein is well-known in the art and is ordinarily used.

In order to overcome the problem with the conventional therapeutic agent, more particularly, the problem of requiring frequent administration of exendin-4 used as a therapeutic agent for diabetes due to the short half-life thereof, the present invention was aimed at increasing the in-vivo half-life of exendin-4, and found that half-life of exendin-4 was dramatically increased when an albumin-binding domain and an anti-FcRn affibody were fused to the exendin-4.

Therefore, in one aspect, the present invention is directed to a long-acting exendin-4 in which an albumin-binding domain (ABD) and an anti-FcRn affibody are fused to exendin-4.

The present invention includes an exendin-4-albumin-binding domain-anti-FcRn affibody fusion protein (hereinafter, referred to as "long-acting exendin-4") having a remarkably increased half-life which is capable of effectively inhibiting the degradation of exendin-4 in vascular endothelial cells by fusing exendin-4 with an albumin-binding domain (ABD) having high binding ability to albumin, and further fusing the exendin-4 with an affibody molecule having high binding ability to human FcRn. The long-acting exendin-4 according to the present invention preferably has a half-life in the plasma of 3 days or longer, more preferably 4 days or longer, even more preferably 5 days or longer, and still even more preferably 6 days or longer.

In the present invention, the exendin-4 constituting the long-acting exendin-4 may be represented by the amino acid sequence of SEQ ID NO: 1, the albumin-binding domain may be represented by the amino acid sequence of SEQ ID NO: 2, and the anti-FcRn affibody may be represented by the amino acid sequence of SEQ ID NO: 3, but the disclosure is not limited thereto.

Exendin-4
(SEQ ID NO: 1)
HGEGTFTSDLSKQMEEEAVRLFIEWLKNGGPSSGAPPPS

ABD
(SEQ ID NO: 2)
LKEAKEKAIEELKKAGITSDYYFDLINKAKTVEGVNALKDEILKA

Anti-FcRn affibody
(SEQ ID NO: 3)
VDAKYAKEFESAAHEIRWLPNLTYDQRVAFIHKLSDDPSQSSELLSEAKKL
NDSQAPK However, in addition to the above-described sequences, in another embodiment, an alternative albumin-binding domain, which is any of various albumin-binding domains constructed by slightly changing the sequence of amino acids based on streptococcal protein G, particularly the G148-GA3 domain, may be applied to the present invention. For example, the following albumin-binding domain may be utilized as well.

ABD of another embodiment (ABD 035)
(SEQ ID NO: 7)
LAEAKVLANRELDKYGVSDFYKRLINKAKTVEGVEALKLHILAALP In another embodiment, an alternative anti-FcRn affibody having the following sequence may be used in the present invention, and in yet another embodiment, an alternative anti-FcRn affibody may be used in the present invention as well.

Anti-FcRn affibody of another embodiment
(SEQ ID NO: 8)
VDAKYAKEQDAAAHEIRWLPNLTFDQRVAFIHKLADDPSQSSELLSEAKKL
NDSQAPK Anti-FcRn affibody of yet another embodiment
(SEQ ID NO: 9)
VDAKYAKEWMRAAHEIRWLPNLTFDQRVAFIHKLEDDPSQSSELLSEAKKL
NDSQAPK Meanwhile, it will be obvious to those skilled in the art that the above sequences can be modified within the ranges equivalent thereto while maintaining the technical features of the present invention.

In the present invention, the exendin-4 and the albumin-binding domain may be linked through a peptide linker, and the albumin-binding domain and an anti-FcRn affibody may be linked through a peptide linker, and the peptide linker may be represented by the amino acid sequence of (GGGGS)$_4$ (SEQ ID NO: 10), but is not limited thereto.

Meanwhile, in the present invention, it was found that the long-acting exendin-4 according to the present invention maintains the blood glucose control function for 12 days or longer when administered alone, and thus the long-acting exendin-4 of the present invention can be used in a one-week to two-week formulation depending on the dose. In addition, administration of the drug once a week for 10 weeks normalizes liver enzyme levels, ameliorates fatty liver, reduces cholesterol in the body, promotes weight loss, and ameliorates all complications of metabolic syndrome, such as cognitive impairment.

In another aspect, the present invention is directed to a pharmaceutical composition for treating metabolic diseases including the long-acting exendin-4 as an active ingredient.

In the present invention, the metabolic disease includes at least one disease selected from the group consisting of diabetes, fatty liver, and obesity, but is not limited thereto.

That is, the present invention may be used for the delay or prevention of hyperglycemia, type 2 diabetes, glucose tolerance impairment (IGT), type 1 diabetes, obesity, or metabolic syndrome, or the progression of diseases from type 2 diabetes, the treatment of metabolic syndrome, the treatment of obesity, or the prevention of overweight, reduction of food intake, increase of energy consumption, weight loss, delay of progression from glucose tolerance impairment to type 2 diabetes; delay of the progression from type 2 diabetes to insulin-requiring diabetes; appetite control; induction of satiety; prevention of weight recovery after successful weight loss; treatment of a disease or condition related to overweight or obesity; treatment of anorexia; treatment of bulimia; treatment of type 2 diabetes, IGT, dyslipidemia, coronary artery disease, or hepatic steatosis, and treatment or prevention of hypoglycemia, insulin-induced hypoglycemia, reactive hypoglycemia, diabetic hypoglycemia, non-diabetic hypoglycemia, hypoglycemia induced by fasting, drug-induced hypoglycemia, hypoglycemia induced by gastrointestinal fusion, hypoglycemia during pregnancy, alcohol-induced hypoglycemia, insulinoma, and Von Gierke disease.

In addition, it was found in the present invention that the cognitive ability of the mice with metabolic diseases was inhibited by a high-fat diet, but this cognitive ability inhibition phenomenon was remarkably alleviated when the long-acting exendin-4 according to the present invention was administered thereto.

Therefore, in another aspect, the present invention provides a pharmaceutical composition for treating cognitive impairment including the long-acting exendin-4 as an active ingredient.

In the present invention, the cognitive impairment may be a degenerative brain disease such as mild cognitive impairment, vascular dementia, or Alzheimer's disease caused by metabolic diseases, but is not limited thereto.

The pharmaceutical composition of the present invention may be provided as a composition that may be combined with the long-acting exendin-4 or a pharmaceutically acceptable carrier or medium thereof. The carrier or medium used may include solvents, dispersants, coatings, absorption accelerators, controlled release agents (i.e., sustained release agents), and one or more inert excipients (starch, polyol, granules, microfine cellulose, microcrystalline cellulose (for example, Cellphere or Cellphere beads), diluents, lubricants, binders, disintegrants, etc.), and the like. If necessary, the tablet formulation of the disclosed composition may be coated using a standard aqueous or non-aqueous method. Examples of excipients for use as pharmaceutically acceptable carriers and pharmaceutically acceptable inert carriers and such additional components include binders, fillers, disintegrants, lubricants, antimicrobial agents, and coating agents, but are not limited thereto.

Acceptable pharmaceutical carriers or media include those used in formulations suitable for oral, rectal, nasal, or parenteral (including subcutaneous, intramuscular, intravenous, intradermal, and transdermal) administration. The compound of the present invention is typically administered parenterally.

Unless otherwise mentioned, the term "treatment" means to reverse or alleviate one or more symptoms of a disorder or disease to which the term is applied or to inhibit or prevent the progress thereof. The term "therapeutic" or "treating" used herein refers to an action of performing treatment when the term "treatment" is defined as above.

The pharmaceutical composition according to the present invention may include an effective amount of long-acting exendin-4 alone, or may further include at least one pharmaceutically acceptable carrier, excipient, or diluent.

As used herein, the term "effective amount" refers to an amount that is sufficient to deliver the desired effect, but is small enough to prevent serious side effects within the scope of medical judgment. The amount of long-acting exendin-4 administered into the body through the composition of the present invention may be appropriately adjusted in consideration of the route of administration and the patient to whom the same is to be administered.

In one aspect based on the animal experiment of the present invention, a single intraperitoneal dose administered to a mouse is 1.6 mg/kg in the case of 50 nmol/kg and 6.4 mg/kg in the case of 200 nmol/kg.

When the above experimental results are applied to the formula in the art used for developing an optimal formulation, the therapeutically effective amount of the present invention (for example, an amount effective for oral administration) may be calculated using the following formula based on a 60 kg adult.

(1.6 *mg* or 6.4 *mg*)*0.08(mouse body surface area conversion index)*60(based on 60 *kg* adult)=7.68 or 30.72 *mg*/day/60 *kg* adult (single administration effective for about 2 weeks)

The composition of the present invention may be administered once every 7 to 14 days, depending on the target subject and dose. The unit dose refers to a unit that is physically separated suitable for unit administration for human and other mammal subjects, and each unit includes an appropriate pharmaceutical carrier, and contains a predetermined amount of the long-acting exendin-4 of the present invention exhibiting a therapeutic effect. The oral dose of the composition of the present invention is 0.0001 to 10 g, preferably 0.001 to 5 g for a single dose. The pharmaceutically effective amount of long-acting exendin-4 for oral administration of the present invention is 0.0001 to 10 g/day. Meanwhile, a dose of Byetta as a conventional protein therapeutic agent for subcutaneous injection is administered at 5 μg or 10 μg twice a day for about 12 weeks. In view of this point, a single subcutaneous injection dose of the present invention is expected to be 0.1 μg to 100 μg, preferably 1 μg to 20 μg. The dose defined above according to the present invention enables administration at a frequency of once a week to once every two weeks. However, the dose will vary depending on the severity of the disease related to metabolic or cognitive ability of the patient and auxiliary active ingredients that are used. The dose range of the present invention does not limit the scope of the present invention in any way.

In addition, the term "pharmaceutically acceptable" used herein refers to a composition that is physiologically acceptable and does not usually cause allergic reactions such as gastrointestinal disorders and dizziness or similar reactions thereto when administered to humans.

The compositions of the present invention may be formulated using methods known in the art to provide rapid, sustained or delayed release of the active ingredient after administration to mammals. The formulation may be in the form of a powder, granule, tablet, emulsion, syrup, aerosol, soft or hard gelatin capsule, sterile injectable solution, or sterile powder. In addition, the composition for preventing or treating metabolic or cognitive diseases according to the present invention may be administered through any of various administration routes, including oral, transdermal, subcutaneous, intravenous or intramuscular administration, the dose of the active ingredient may be appropriately selected according to various factors such as the route of administration, the patient's age, gender and weight, and the severity of the disease of the patient, and the composition for preventing or treating metabolic and/or cognitive disorders according to the present invention may be administered in conjunction with a known compound having an effect of preventing, ameliorating or treating symptoms of metabolic and/or cognitive-ability-related disorders.

In another aspect, the present invention is directed to the use of the long-acting exendin-4 for the prevention or treatment of metabolic diseases and/or cognitive impairment.

As used herein, the term "prevention" relates to averting, delaying, impeding, or hindering to relieve a disease.

As used herein, the term "treatment" relates to caring for a subject suffering from a disease in order to ameliorate, cure or reduce symptoms of the disease or reduce or stop the progression of the disease.

In another aspect, the present invention is directed to a method for preventing, treating or alleviating metabolic diseases and/or cognitive impairment including administering a pharmaceutically effective amount of the long-acting exendin-4 to a subject in need of prevention or treatment of metabolic diseases and/or cognitive impairment, or improvement of metabolic health or cognitive ability.

Since the pharmaceutical composition and the administration method used in the method of preventing or treating metabolic diseases and/or cognitive impairment have been described above, descriptions in common therewith are omitted in order to avoid excessive complexity of the present specification.

Meanwhile, the subject to which the composition for preventing or treating metabolic diseases and/or cognitive impairment can be administered includes all animals including humans. For example, the subject may be an animal such as a dog, cat, or mouse.

In another aspect, the present invention is directed to the use of the long-acting exendin-4 for the treatment, prevention or alleviation of metabolic diseases.

In another aspect, the present invention is directed to the use of the long-acting exendin-4 for the preparation of a drug for treating or preventing cognitive impairment or for improving cognitive ability.

In another aspect, the present invention is directed to a food composition for preventing or ameliorating metabolic diseases including the long-acting exendin-4 as an active ingredient.

In the present invention, the metabolic disease may include at least one disease selected from the group consisting of diabetes, fatty liver, and obesity, but is not limited thereto.

In another aspect, the present invention is directed to a food composition for improving cognitive ability including the long-acting exendin-4 as an active ingredient.

The term "cognitive ability" refers to the ability to acquire and use knowledge such as comprehension, thinking, memory, and judgment.

The food composition may be used easily as, for example, a main or auxiliary food ingredient, a food additive, or a functional beverage to exhibit an effect on ameliorating or preventing metabolic diseases such as obesity, fatty liver and diabetes and/or improving cognitive ability, but is not limited thereto.

The term "food" refers to a natural product or processed product containing at least one nutrient, preferably in a state that can be digested directly through a certain extent of processing, and generally includes all a food, food additive, health functional food and functional beverage.

Examples of the food to which the composition for food according to the present invention can be added include various foods, beverages, gums, teas, vitamin complexes, functional foods and the like. In addition, the food according to the present invention includes special nutritional foods (e.g., formulated milk, infant food, and baby food), processed meat products, fish products, tofu, muk, noodles (e.g., ramen, noodles, etc.), bread, health supplements, seasonings (e.g. soy sauce, miso, red pepper paste, mixed sauce, etc.), sauces, confectioneries (e.g. snacks), candy, chocolate, gums, ice cream, dairy products (e.g. fermented milk, cheese, etc.), other processed foods, kimchi, pickled foods (various kimchi, pickles, etc.), beverages (e.g., fruit beverages, vegetable beverages, soy milk, fermented beverages, etc.), and natural seasonings (e.g., ramen seasoning, etc.), but are not limited thereto. The food, beverage or food additive may be produced through a conventional production method.

As used herein, the term "health functional food" refers to a food provided with added value by imparting a function to the food for a specific purpose, or a food that is designed and processed to enable a food composition to sufficiently express body control functions such as bio-defense rhythm control, disease prevention and disease recovery, in the body using physical, biochemical, and biotechnological methods. The functional food may include a cytologically acceptable food supplement and may further include an appropriate carrier, excipient and diluent commonly used for the preparation of functional foods.

As used herein, the term "functional beverage" is a generic term referring to a beverage drunk to quench thirst thereof or to enjoy the taste and may further include, in addition to a composition for ameliorating or preventing symptoms of metabolic diseases and/or cognitive impairment as an essential ingredient at the predetermined ratio, additional ingredients such as various flavoring agents or natural carbohydrates, like ordinary beverages. There is no particular limitation as to such other ingredients.

In addition to the ingredients described above, the food composition for ameliorating or preventing of symptoms of metabolic disease and/or cognitive impairment according to the present invention may include various nutrients, vitamins, minerals (electrolytes), flavoring agents such as synthetic and naturals flavoring agents, colorants and fillers (such as cheese and chocolate), pectic acid and salts thereof, alginic acid and salts thereof, organic acids, protective colloid thickeners, pH adjusters, stabilizers, preservatives, glycerin, alcohols, and carbonates used in carbonated beverages. These components may be used alone or in combination.

The food containing the food composition of the present invention may include the composition according to the present invention in an amount of 0.001% to 100% by weight, preferably 1% to 99% by weight, based on the total weight of the food. A beverage may include the composition in a ratio of 0.001 g to 10 g, preferably 0.01 g to 1 g, based on 100 ml. However, in the case of long-term intake for the purpose of health and hygiene or for the purpose of health management, the amount may be below the range defined above, and the active ingredient may be used in an amount over the above range because there is no problem in terms of safety.

The food composition of the present invention may be prepared in the form of a composition suitable for human or animal consumption by adding the long-acting exendin-4 independently or adding the long-acting exendin-4 to an acceptable carrier. That is, the food composition may be added to and used in foods that do not contain other substances for ameliorating metabolic diseases and/or improving cognitive ability, and foods that already contain some substances for ameliorating metabolic diseases and/or improving cognitive ability. Examples of the carrier that can be used in the food composition of the present invention include extenders, high-fiber additives, encapsulating agents, lipids, and the like, and examples of such a carrier are well known in the art. The food of the present invention may be lyophilized or encapsulated, or may be in the form of a suspension or dry powder.

Meanwhile, in the present invention, it was found that long-acting exendin-4 can be easily produced using a recombinant vector and a recombinant microorganism.

In another aspect, the present invention is directed to a recombinant vector including a nucleic acid encoding exendin-4, a nucleic acid encoding an albumin-binding domain (ABD), and a nucleic acid encoding an anti-FcRn affibody.

In the present invention, the nucleic acid encoding exendin-4 may be represented by the amino acid sequence of SEQ ID NO: 4, the nucleic acid encoding the albumin-binding domain (ABD) may be represented by the amino acid sequence of SEQ ID NO: 5, and the nucleic acid encoding the anti-FcRn affibody may be represented by the amino acid sequence of SEQ ID NO: 6.

```
Nucleic acid encoding exendin-4
                                   (SEQ ID NO: 4)
CACGGCGAGGGCACCTTTACCAGCGACCTGAGCAAGCAAATGGAAGAGGAA

GCGGTTCGTCTGTTTATTGAGTGGCTGAAAAATGGCGGTCCGAGCAGCGGT

GCTCCGCCGCCGAGC

Nucleic acid encoding albumin-binding domain
                                   (SEQ ID NO: 5)
CTGAAAGAGGCGAAGGAAAAAGCGATCGAGGAACTGAAGAAAGCGGGTATT

ACCAGCGACTACTATTTCGATCTGATCAACAAGGCGAAAACCGTGGAGGGT

GTTAACGCGCTGAAGGACGAAATTCTGAAAGCG

Nucleic acid encoding anti-FcRn affibody
                                   (SEQ ID NO: 6)
GTGGATGCGAAGTATGCGAAAGAGTTCGAAAGCGCGGCGCATGAGATCCGT

TGGCTGCCGAACCTGACCTATGATCAGCGTGTTGCGTTTATTCACAAACTG

AGCGACGATCCGAGCCAGAGCAGCGAACTGCTGAGCGAAGCGAAAAAACTG

AACGATAGCCAAGCGCCGAAG
```

In another aspect, the present invention is directed to a recombinant microorganism for producing long-acting exendin-4 introduced with the recombinant vector. The recombinant microorganism may be *E. coli*, but is not limited thereto.

The recombinant vector according to the present invention may be constructed as a vector for cloning or expression, and may be constructed as a vector for use with prokaryotic or eukaryotic cells as host cells.

As used herein, the term "vector" refers to a recombinant vector capable of expressing a target protein in a suitable host cell, and means a nucleic acid construct including essential regulatory elements operatively linked to express a nucleic acid insert. The present invention is capable of producing a recombinant vector containing a nucleic acid encoding long-acting exendin-4, and enables long-acting exendin-4 of the present invention to be obtained by transforming or transfecting host cells with the recombinant vector.

The nucleic acid encoding exendin-4 according to the present invention is operatively linked to a promoter. The term "operatively linked" as used herein means a functional linkage between a polynucleotide expression regulation sequence (e.g., a promoter, signal sequence, ribosome-binding site, transcription termination sequence) and another polynucleotide sequence. Accordingly, the regulation sequence can regulate transcription and/or translation of other nucleotide sequences.

As used herein, the term "promoter" refers to a DNA region that includes a polymerase-binding site and binds to an upstream untranslated nucleic acid sequence of the coding region, that is, polymerase, having activity to initiate transcription of promoter downstream genes into mRNA, to initiate transcription of a gene and is located at the 5' position of the mRNA transcription initiation site.

When the vector according to the present invention is a recombinant vector and a prokaryotic cell is used as a host, the vector generally includes a potent promoter capable of initiating transcription (such as a tac promoter, lac promoter, lacUV5 promoter, lpp promoter, pLλ promoter, pRA promoter, rac5 promoter, amp promoter, recA promoter, SP6 promoter, trp promoter, trc promoter, phoA promoter araBAD promoter, T5 promoter or T7 promoter), a ribosome-binding site to initiate translation, and a transcription/translation termination sequence.

In addition, the vector that can be used in the present invention may be produced by manipulating plasmids often used in the art (e.g., pSC101, pGV1106, pACYC177, ColE1, pKT230, pME290, pBR322, pUC8/9, pUC6, pBD9, pHC79, pIJ61, pLAFR1, pHV14, pGEX series, pET series, pPICZα series, or pUC19), phages (e.g., λgt4λB, λ-Charon, λΔz1, M13 and the like), or viruses (e.g., SV40 and the like), but are not limited thereto.

Meanwhile, when the vector according to the present invention is a recombinant vector and a eukaryotic cell is used as a host, a promoter derived from the genome of mammalian cells (e.g., a metallothionein promoter) or a promoter derived from mammalian virus (e.g., adenovirus late promoter, vaccinia virus 7.5K promoter, SV40 promoter, cytomegalovirus promoter, or HSV tk promoter) may be used, and the vector generally has a polyadenylation sequence (e.g., bovine growth hormone terminator and SV40-derived polyadenylation sequence) as a transcription termination sequence.

In addition, the recombinant vector of the present invention includes an antibiotic resistance gene commonly used in the art as a selection marker, and the antibiotic resistance gene may, for example, be a gene resistant to ampicillin, gentamicin, carbenicillin, chloramphenicol, streptomycin, kanamycin, geneticin, neomycin and tetracycline.

The recombinant vector of the present invention may further include another sequence as necessary in order to facilitate purification of the recovered target protein, that is, long-acting exendin-4. The sequence that may be additionally included may be a tag sequence for protein purification, for example, glutathione S-transferase (Pharmacia, USA), maltose-binding protein (NEB, USA), FLAG (IBI, USA), SUMO, hexahistidine, and the like. However, the types of sequences required for purification of the target protein are not limited to the examples described above. The fusion protein expressed by the recombinant vector containing the tag sequence described above may be purified through affinity chromatography. For example, when glutathione-S-transferase is fused, glutathione, which is a substrate for this enzyme, may be used, and when hexahistidine tags are used, a desired target protein can be easily recovered using a Ni-NTA column. A recombinant microorganism transformed with the vector may be constructed using the recombinant vector containing the polynucleotide encoding the long-acting exendin-4.

As used herein, the term "transformation" means introducing DNA into host cells and making the DNA replicable using a chromosomal factor or chromosomal integration, and is defined as a phenomenon in which genetic changes are artificially induced by introducing external DNA into cells.

The transformation method of the present invention may be realized by any transformation method and may be easily performed in accordance with a conventional method in the art. In general, the transformation method includes $CaCl_2$ precipitation, a Hanahan method, which uses dimethyl sulfoxide (DMSO) as a reducing material for $CaCl_2$ precipitation to increase efficiency, electroporation, calcium phosphate precipitation, protoplast fusion, agitation using silicon carbide fibers, agrobacteria-mediated transformation, transformation using PEG, dextran sulfate, or lipofectamine, and drying/inhibition-mediated transformation.

The method for transforming the recombinant vector containing a nucleic acid encoding long-acting exendin-4 according to the present invention is not limited to the examples described above, and any transformation or transfection method commonly used in the art can be used without limitation.

The transformant of the present invention can be obtained by introducing a recombinant vector containing a nucleic acid encoding, as a target nucleic acid, long-acting exendin-4, into a host cell.

The host suitable for the present invention is not particularly limited, as long as it allows the nucleic acid of the present invention to be expressed. Specific examples of the host that can be used in the present invention include bacteria of the genus *Escherichia* such as *E. coli*; bacteria of the genus *Bacillus* such as *Bacillus subtilis*; bacteria of the genus *Pseudomonas* such as *Pseudomonas putida*; yeasts such as *Pichia pastoris, Saccharomyces cerevisiae*, and *Schizosaccharomyces pombe*; insect cells such as *Spodoptera frugiperda* (SF9); and animal cells such as CHO, COS, and BSC, but are not limited thereto.

The present invention provides a method of producing long-acting exendin-4 with an increased in-vivo half-life including (a) culturing the recombinant microorganism, (b) disrupting the cultured recombinant microorganism to obtain long-acting exendin-4, and (c) purifying the long-acting exendin-4.

Hereinafter, the present invention will be described in more detail with reference to examples. However, it will be obvious to those skilled in the art that these examples are provided only for illustration of the present invention, and should not be construed as limiting the scope of the present invention.

Example 1. Construction of Plasmid for Expression of SUMO-Exendin-4-ABD-aFaff

For the construction of the pET28a-SUMO-Exendin-4-ABD-aFaff plasmid for expressing SUMO-Exendin-4-ABD-aFaff, the expression gene (570 bp) of Exendin-4-ABD-aFaff was synthesized by GenScript, digested with restriction enzymes Nde1 and EcoR1, and then inserted into a pET28a-SUMO vector using T4 ligase. Likewise, for pET28a-SUMO-Exendin-4, pET28a-SUMO-Exendin-4-ABD and pET28a-SUMO-Exendin-4-aFaff and SUMO-Exendin-4, an expression gene of SUMO-Exendin-4 (441 bp), an expression gene of Exendin-4-ABD (336 bp), and an expression gene of Exendin-4-aFaff (375 bp) were synthesized by GenScript, and digested with restriction enzymes Nde1 and EcoR1, and then, using T4 ligase, the SUMO-Exendin-4 gene was inserted into the pET28a vector, and Exendin-4-ABD and Exendin-4-aFaff genes were inserted into the pET28a-SUMO vector. The produced expression plasmids of Exendin-4-ABD-aFaff, Exendin-4, Exendin-4-ABD and Exendin-4-aFaff were transfected into DH5a *E. coli*.

The amino acid sequences used in the present invention are given as below, and the Exendin-4, ABD and anti-FcRn affibody are linked via a (GGGGS)$_4$ linker.

```
Exendin-4
                                        (SEQ ID NO: 1)
HGEGTFTSDLSKQMEEEAVRLFIEWLKNGGPSSGAPPPS ABD
                                        (SEQ ID NO: 2)
LKEAKEKAIEELKKAGITSDYYFDLINKAKTVEGVNALKDEILKA Anti-FcRn affibody
                                        (SEQ ID NO: 3)
VDAKYAKEFESAAHEIRWLPNLTYDQRVAFIHKLSDDPSQSSELLSEAKKL

NDSQAPK
```

Example 2. Expression and Purification of Exendin-4-ABD-aFaff

Figure 2:
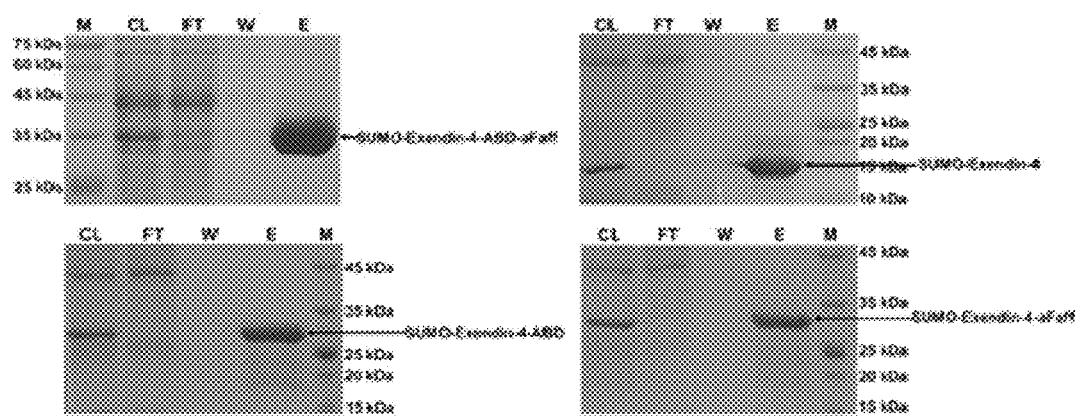
FIG. 2 shows the expression of exendin-4-ABD-aFaff, exendin-4, exendin-4-aFaff and exendin-ABD, detected by Coomassie staining.

For the expression of Exendin-4-ABD-aFaff, pET28A-SUMO-Exendin-4-ABD-aFaff was transfected into BL21, a productive *E. coli* strain and then selectively cultured on LB agar medium containing kanamycin (80 μg/mL). Then, one colony grown in agar medium was inoculated into 50 mL of liquid LB medium and cultured overnight at 37° C. at a rotational speed of 250 rpm. The next day, this starter culture was added to 1 L of high-capacity LB medium containing kanamycin and cultured under the same conditions. When the absorbance of the culture solution at 600 nm reached 1, IPTG (final concentration: 0.5 mM) was added to the culture solution, followed by further culture for 4 hours. After the culture, the *E. coli* cells were suspended in 60 mL of a 20 mM phosphate buffer solution (300 mM NaCl, 1% leupeptin and 1% soybean protease inhibitor (Sigma Aldrich), pH 7), and were disrupted using an ultrasonic disruptor. The disrupted *E. coli* solution thus obtained was centrifuged (at 4,000 rpm for 20 minutes), and then the supernatant was purified using Talon resin (Clontech, Mountain View, CA). During the purification, the supernatant was washed with phosphate buffer, and SUMO-Exendin-4-ABD-aFaff protein was obtained using an elution buffer (20 mM PBS, 300 mM NaCl, 300 mM imidazole, pH 7). Exendin-4, Exendin-4-ABD and Exendin-4-aFaff were also produced using the same expression and purification methods as in the case of Exendin-4-ABD-aFaff. The expression and purification of Exendin-4-ABD-aFaff, Exendin-4, Exendin-4-ABD, and Exendin-4-aFaff were detected by Coomassie staining (FIG. 2).

Example 3. Effect of Long-Acting Exendin-4 (Exendin-4-ABD-aFaff) on Improvement of Blood Sugar 3-1. Short-Term Changes in Blood Sugar Levels 3-week-old male C57BL/6J mice were purchased from Jung-Ang Lab, Animal, Inc. and bred in the animal laboratory of Gyeongsang National University. After feeding 60% Kcal fat (Research Diets, Inc., USA) for 12 weeks, the mice were divided into 3 groups (10 mice per group) and fasted (about 14 hours) one day before injection of the drug. At 9 am, 0.9% normal saline, Exendin-4 (50 nmol/kg; 0.9 mg/kg), and Exendin-4-ABD-aFaff (50 nmol/kg; 1.6 mg/kg) were intraperitoneally injected into the mice in each group. One hour after injection, a glucose tolerance test was performed. After intraperitoneal injection of D-glucose (2 g/kg), blood was collected from the tail of each mouse at 30-minute intervals for 2 hours, blood glucose was measured using an Accu-Check glucometer (A), and the area under the curve (AUC) indicating the efficacy of the drug was measured (B).

Figure 3:
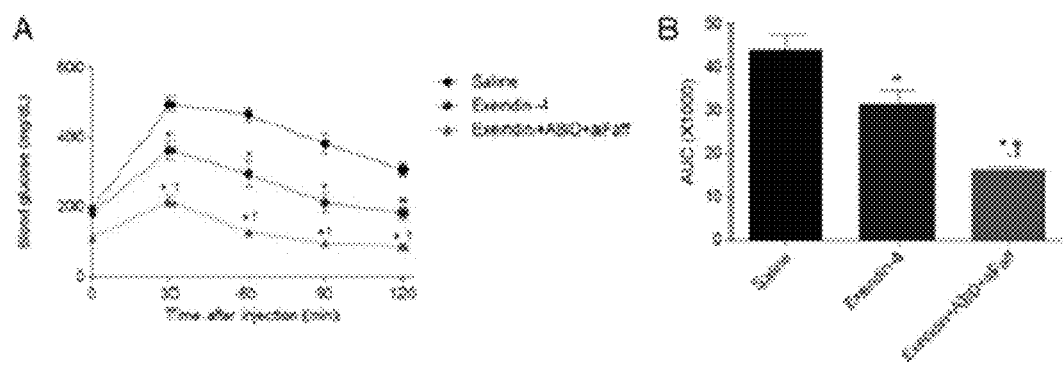
FIG. 3 in graph A shows the short-term change in blood glucose over time upon a single administration of exendin-4-ABD-aFaff and exendin-4, and in graph B shows the area under the curve thereof.

As a result, it can be seen from FIG. 3 that with regard to the effect of improving insulin resistance in high-fat-diet-induced obese mice, single administration of long-acting Exendin-4 exerts a glucose tolerance effect of 50% or more of the blood glucose improvement effect of a conventional Exendin-4 within 2 hours.

3-2. Long-Term Changes in Blood Sugar Levels 3-week-old male C57BL/6J mice were purchased from Jung-Ang Lab, Animal, Inc. and bred in the animal laboratory of Gyeongsang National University. After feeding 60% Kcal fat (Research Diets, Inc., USA) for 14 weeks, the mice were divided into 5 groups (7 mice per group) and the drug was injected into the mice in each group. At 10 am, 0.9% normal saline, exendin-4 (0.9 mg/kg, 3.6 mg/kg), and exendin-4-ABD-aFaff (1.6 mg/kg, 6.4 mg/kg) were intraperitoneally injected into the mice in each group. Then, blood was collected from the tail of each mouse for 2 weeks, blood glucose was measured using an Accu-Check glucometer (A), and changes in body weight caused by drug administration were observed (B).

Figure 4:
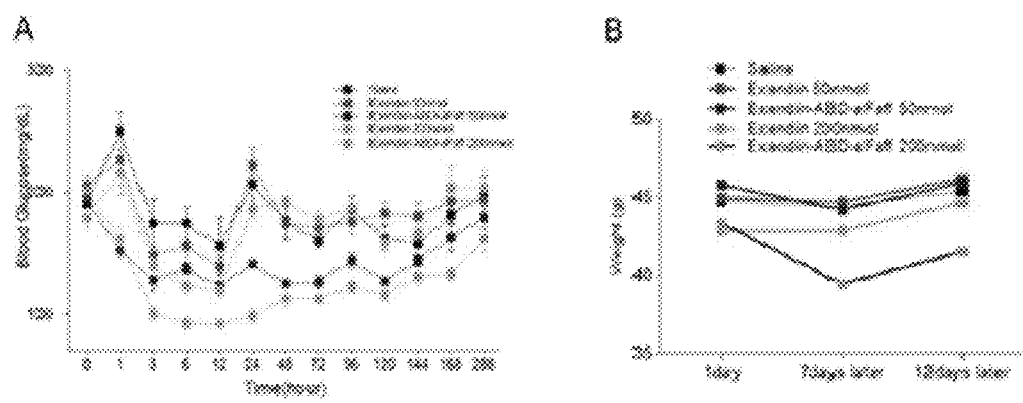
FIG. 4 in graph A shows the long-term change in blood glucose level over time upon a single administration of exendin-4-ABD-aFaff and exendin-4, and in graph B shows the resulting change in weight.

As a result, it can be seen from FIG. 4 that the mice injected once intraperitoneally with Exendin-4 (200 nmol/kg; 3.6 mg/kg) maintained low blood glucose only for about 12 hours and exhibited no weight loss effect, whereas the mice injected once with Exendin-4-ABD-aFaff (200 nmol/kg; 6.4 mg/kg) maintained low blood sugar for 12 days and exhibited an excellent weight loss effect.

3-3. Improvement in Persistence of Exendin-4-ABD-aFaff (Synergistic Effect)

In the present invention, whether or not the Exendin-4-ABD-aFaff can contribute to the sustainment of the metabolic disease treatment effect of Exendin-4 for a remarkably long time was determined, and the synergistic effect of such a combination was compared with that of a combination of exendin-4 only with aFaff, or a combination of Exendin-4 only with ABD.

For this purpose, 3-week-old male C57BL/6J mice were purchased from Jung-Ang Lab, Animal, Inc. and bred in the animal laboratory of Gyeongsang National University. After feeding 60% Kcal fat (Research Diets, Inc., USA) for 14 weeks, the mice were divided into 5 groups (5 to 7 mice per group) and the drug was injected into the mice in each group (without fasting). At 10 am, 0.9% normal saline, Exendin-4 (EX, 200 nmol/kg; 3.6 mg/kg), Exendin-4-aFaff (EX-AFaff, 200 nmol/kg; 4.8 mg/kg), Exendin-4-ABD (EX-ABD, 200 nmol/kg; 4.8 mg/kg), and Exendin-4-ABD-aFaff (EX-ABD- AFaff, 200 nmol/kg; 6.4 mg/kg) were intraperitoneally injected into the mice in each group. Then, blood was collected from the tail of each mouse for 12 days, blood glucose was measured using an Accu-Check glucometer (A), and changes in body weight caused by drug administration were observed (B).

Figure 5:
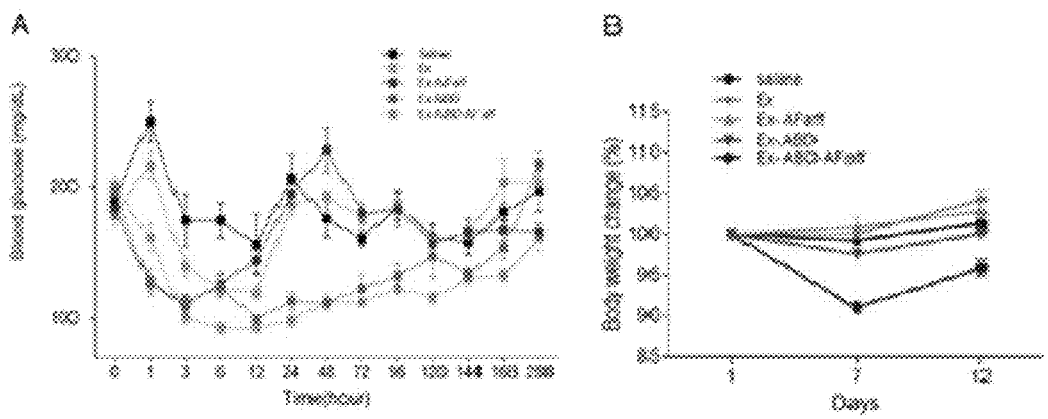
FIG. 5 in graph A shows a comparison of the long-term change in blood glucose level over time upon a single administration of exendin-4, exendin-4-ABD-aFaff, exendin-4-ABD and exendin-4-aFaff, and in graph B shows the resulting change in weight.

As a result, it can be seen from FIG. 5 that the mice intraperitoneally injected with Exendin-4-ABD-aFaff once maintained much lower blood glucose than that of the mice not treated with the drug for about 12 days. It can be seen that Exendin-4-ABD-aFaff advantageously maintained low blood sugar for 12 days, whereas Exendin-4-aFaff did not exhibit a sufficient effect during the first 1-5 days after intraperitoneal injection and Exendin-4-ABD rapidly increased blood sugar after showing effect for 7 days after intraperitoneal injection. In addition, regarding the weight-loss effect, mice injected once intraperitoneally with Exendin-4, Exendin-4-aFaff, or Exendin-4-ABD exhibited no change in body weight, whereas mice injected with Exendin-4-ABD-aFaff exhibited no rapid increase in body weight caused by high-fat diet but exhibited an excellent weight-loss effect. Based on these experimental results, it can be seen that Exendin-4-ABD-aFaff has a remarkably increased plasma half-life compared to conventional long-acting Exendin-4 including Exendin-4-ABD, and that it is possible to maintain a normal blood glucose level, even through administration as seldom as once every two weeks, compared to administration at a maximum interval of once a week for a conventional long-acting formulation. In addition, based thereon, it can be inferred that the remarkable increase in the residence time of Exendin-4-ABD-aFaff in the body promises greater effectiveness not only in the treatment of diabetes but also in the treatment of diabetes complications.

3-4. Comparison of Changes in Blood Glucose Levels Between High-Fat-Diet and Normal-Diet Groups 3-week-old male C57BL/6J mice were purchased from Jung-Ang Lab, Animal, Inc. and bred in the animal laboratory of Gyeongsang National University. After normal diet or feeding 60% Kcal fat (Research Diets, Inc., USA) for 16 weeks, the mice were divided into 7 groups (7-12 mice per group) and the drug was intraperitoneally injected into the mice in each group once a week for 10 weeks. At 10 am, 0.9% normal saline, Exendin-4 (0.9 mg/kg, 3.6 mg/kg), and Exendin-4-ABD-aFaff (1.6 mg/kg, 6.4 mg/kg) were intraperitoneally injected into the mice in each group. After fasting the day before, blood was collected from the tail of each mouse, and blood glucose was measured with an Accu-Check glucometer (A). The mice were anesthetized, and the serum extracted through the left ventricle was sent to Green Cross Co., Ltd. for blood glucose analysis. Insulin analysis was performed using a mouse insulin ELISA kit purchased from Shibayagi, Japan.

Figure 6:
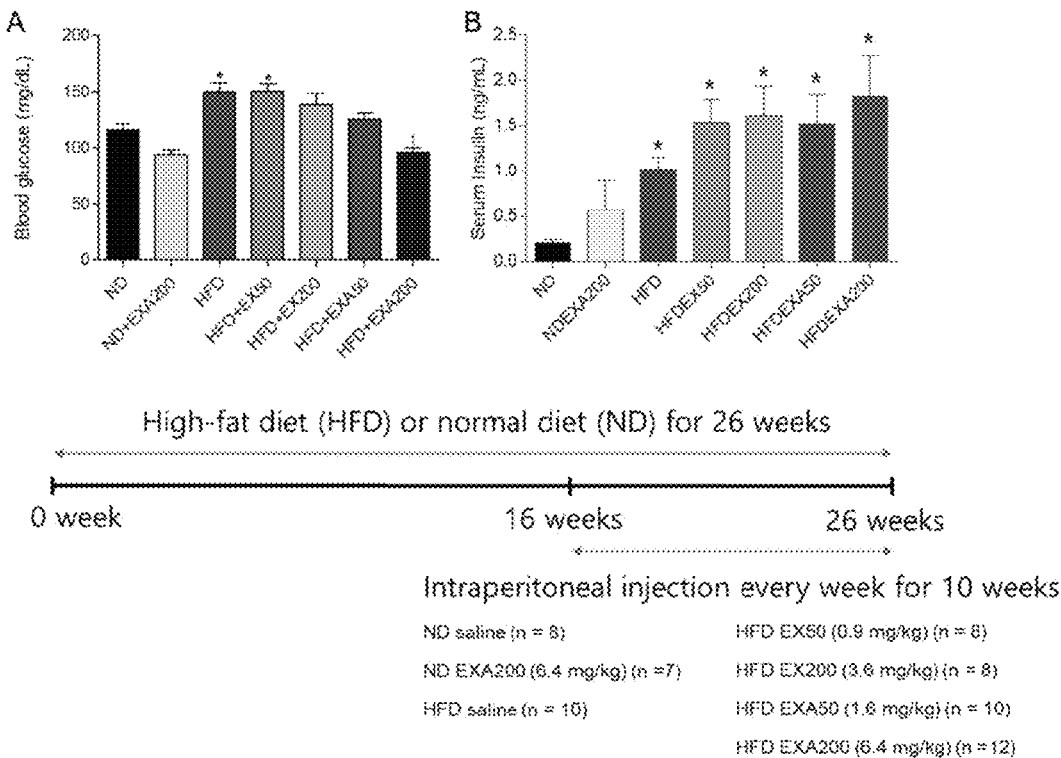
FIG. 6 in graph A shows the change in blood glucose depending on the concentration of administered exendin-4-ABD-aFaff and exendin-4 in high-fat-diet or normal-diet mice, and in graph B shows the change in blood insulin.

As a result, it can be seen from FIG. 6 that the blood glucose of the high-fat-diet (HFD) mice was higher than that of the normal-diet (ND) mice, but the blood glucose of the mice administered with Exendin-4-ABD-aFaff (200 nmol/kg; 6.4 mg/kg) was statistically significantly decreased. Here, the blood glucose of the mice administered with Exendin-4 was not decreased, which demonstrates the superior effect of Exendin-4-ABD-aFaff. In addition, in the normal diet (ND) mice, there was no great change in blood sugar even after long-term administration of Exendin-4-ABD-aFaff, which means that the risk of inducing hypoglycemic shock was low. The serum insulin concentration was increased in both the high-fat diet group and the drug-administered high-fat diet group, but not the normal-diet mice. The reason for the increase in blood insulin concentration in the high-fat diet mouse group is considered to be due to the action of increasing the insulin secretion of pancreatic cells, which is the mechanism of action of Exendin-4.

3-5. Glucose Tolerance Test and Insulin Tolerance Test

The glucose tolerance test and insulin tolerance test upon the administration of Exendin-4-ABD-aFaff and Exendin-4 were conducted on the animal experimental groups of Example 3-4.

The glucose tolerance test(GTT) was performed as follows. D-glucose (2 g/kg) was intraperitoneally injected at 9 am after fasting a day before (about 14 hours), blood was collected from the tail of each mouse at 30-minute intervals for 2 hours, blood glucose was measured using an Accu-Check glucometer, and the area under the curve (AUC) indicating the efficacy of the drug was calculated.

The insulin tolerance test was performed as follows. Insulin (0.75 U/kg, Humulin-R, Eli Lilly, USA) was intraperitoneally injected at 2 pm, blood was collected from the tail of each mouse every 15 minutes for 1 hour, blood glucose was measured using an Accu-Check glucometer, and the area under the curve (AUC) indicating the efficacy of the drug was calculated.

Figure 7:
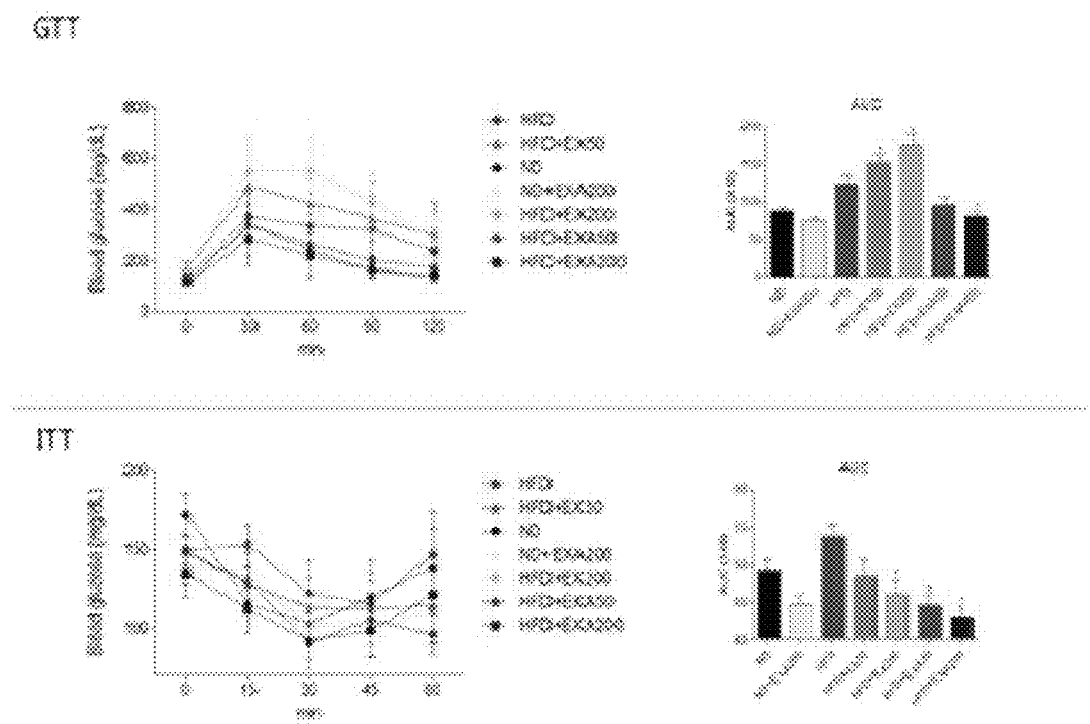
FIG. 7 shows the results of a glucose tolerance test and an insulin tolerance test depending on the concentration of administered exendin-4-ABD-aFaff and exendin-4.

As a result, it can be seen from FIG. 7 that in the glucose tolerance test, the glucose tolerance was decreased only in the mice administered with Exendin-4-ABD-aFaff, and in the insulin tolerance test, the insulin tolerance was improved in the mice administered with Exendin-4 and Exendin-4-ABD-aFaff. Meanwhile, it can be seen that the mouse group administered with Exendin-4-ABD-aFaff (200 nmol/kg; 6.4 mg/kg) exhibited improved glucose tolerance and increased insulin sensitivity.

Example 4. Effect of Long-Acting Exendin-4 (Exendin-4-ABD-aFaff) on Amelioration of Fatty Liver A test to determine the effect of administration of Exendin-4-ABD-aFaff and Exendin-4 on amelioration of fatty liver was performed on the animal experimental groups of Example 3-4.

Example 4-1. Changes in Liver Enzyme Levels

Each mouse was anesthetized, whole blood was collected from the left ventricle thereof using a 1 ml syringe, and then serum and blood cells were separated using a centrifuge. The serum was sent to Green Cross Co., Ltd. for analysis of two liver enzymes, ALT and AST.

Figure 8:
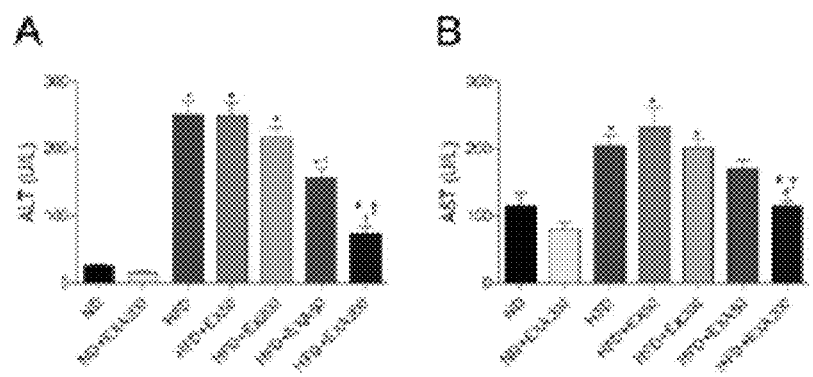
FIG. 8 in graphs A and 8B shows the result of analysis of changes in ALT and AST, respectively, which are liver enzyme levels, depending on the concentration of administered exendin-4-ABD-aFaff and exendin-4.

As a result, it can be seen from FIG. 8 that both liver enzymes increased in the high-fat-diet mice, but levels of both enzymes decreased in mice administered with Exendin-4-ABD-aFaff, and levels of both enzymes hardly decreased in mice administered with Exendin-4.

Example 4-2. Detection of Fat Accumulation in Liver Cells and Observation of Changes in Liver Size and Weight After intramuscular injection of the anesthetic Zoletil (Virbac Laboratories), cardiac perfusion was performed with a fixative (4% paraformaldehyde in 0.1 M phosphate-buffered saline (PBS). The liver was extracted and then additionally placed in the fixative for 6 hours. Paraffinic liver sections were formed for Hematoxylin & Eosin (H&E) staining, frozen and cut, subjected to fluorescence staining with Nile Red (Sigma) for observation of the fat mass in hepatocytes, and then observed under optical and fluorescence microscopes.

Figure 9:
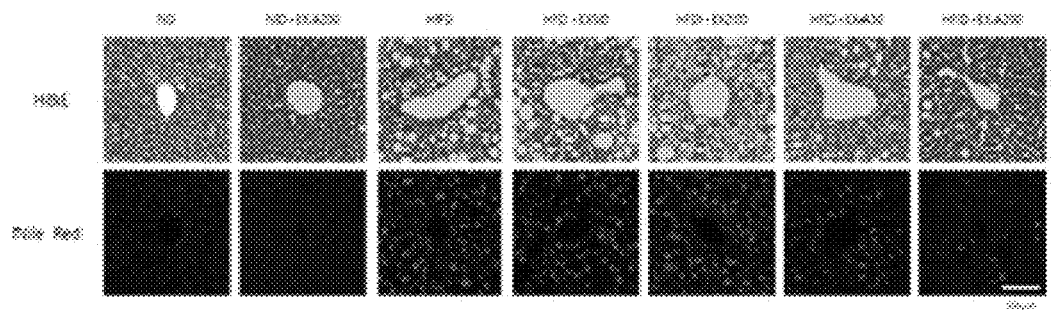
FIG. 9 shows the accumulation of fat in liver cells depending on the concentration of administered exendin-4-ABD-aFaff and exendin-4, observed by H&E staining and Nile red fluorescence staining.

As a result, as shown in FIG. 9, a large number of hepatocytes having high amounts of accumulated fat were observed in the liver tissue of the high-fat-diet mice. In this case, it was found that fat accumulation in the liver tissue administered with Exendin-4 was not alleviated, but fat accumulation in the liver tissue administered with Exendin-4-ABD-aFaff was alleviated in a concentration-dependent manner.

Meanwhile, in order to observe changes in liver size and weight, whole blood was collected from the left ventricle, after which the liver was extracted and the weight thereof was measured.

Figure 10:
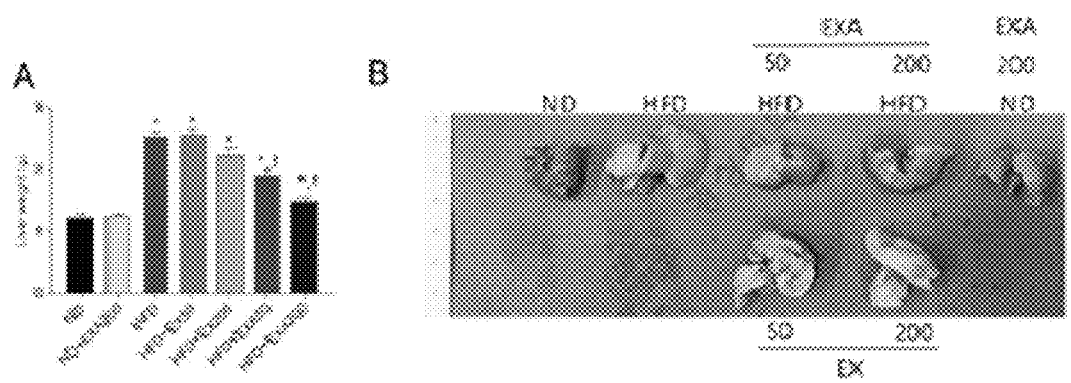
FIG. 10 in graph A and in image B shows results of quantitative analysis and visual observation, respectively, of changes in liver size and weight depending on the concentration of administered exendin-4-ABD-aFaff and exendin-4.

As a result, it can be seen from FIG. 10 that the liver weight of the high-fat-diet mice was increased to about double that of the normal-diet mice, and the weight of the liver was decreased depending on the concentration of administered Exendin-4-ABD-aFaff. When observed with the naked eye, the livers of the high-fat-diet mice were larger than those of the normal-diet mice and were yellow, but the fatty livers of mice administered with Exendin-4-ABD-aFaff had a color similar to normal livers and a much smaller size in comparison with the livers of the high-fat-diet mice. However, it can be seen that the livers of mice administered with Exendin-4 remained yellow and hardly decreased in size.

Example 4-3. Measurement of Nonalcoholic Fatty Liver Disease Activity Score

In order to measure the non-alcoholic fatty liver disease activity score, the liver tissue sections of Example 4-2 were observed with an optical microscope, the levels of steatosis, lobular inflammation, and hepatocellular ballooning were measured, and the sum of respective measured values was calculated.

TABLE 1

| NAFLD activity score | NASH fibrosis stage |
|---|---|
| Steatosis | Stage 0 |
| <5%: 0 5-33%: 1 34-66%: 2 >66%: 3 | No fibrosis Stage 1 Zone 3 perisinusodial fibrosis |
| Lobular Inflammation | Mild-1a Moderate-1b |
| None: 0 <2: 1 | Portal/periportal-1c Stage 2 |
| 2-4: 3 >4: 4 Ballooning of | Perisinusoidal and portal/ periportal fibrosis Stage 3 |
| hepatocytes | Bridging fibrosis |
| None: 0 | Stage 4 |
| Few ballooned: 1 Many ballooned: 2 NASH score (0-8) | Cirrhosis |
| <3: not NASH ≥5: NASH | |

Figure 11:
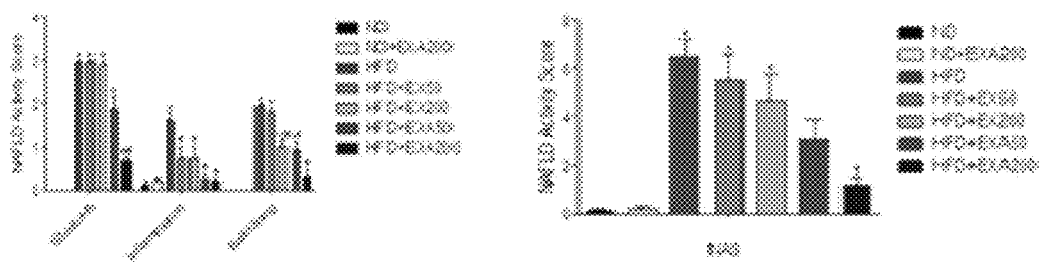
FIG. 11 shows nonalcoholic fatty liver disease activity score of steatosis, lobular inflammation, and hepatocellular ballooning depending on the concentration of administered exendin-4-ABD-aFaff and exendin-4.

As a result, it can be seen from FIG. 11 that steatosis, lobular inflammation, and hepatocellular ballooning were not observed in the liver tissue of the normal-diet mice, but all three pathological characteristics were increased in the liver tissue of the high-fat-diet mice. On the other hand, it can be seen that the non-alcoholic fatty liver disease activity decreased the most in the high-fat-diet mice administered with Exendin-4-ABD-aFaff (200 nmol/kg; 6.4 mg/kg), but this decrease was not observed in the mice administered with Exendin-4.

Example 5. Effect of Long-Acting Exendin-4 (Exendin-4-ABD-aFaff) on Alleviation of Obesity A test to determine the effect of alleviation of obesity depending on the concentration of administered Exendin-4-ABD-aFaff and Exendin-4 was performed on the animal experimental group of Example 3-4.

5-1. Decreased Appetite, Weight Loss, and Body Fat Loss

Feed intake and body weight were measured every week after injection of the drug into the animal experimental group.

Figure 12:
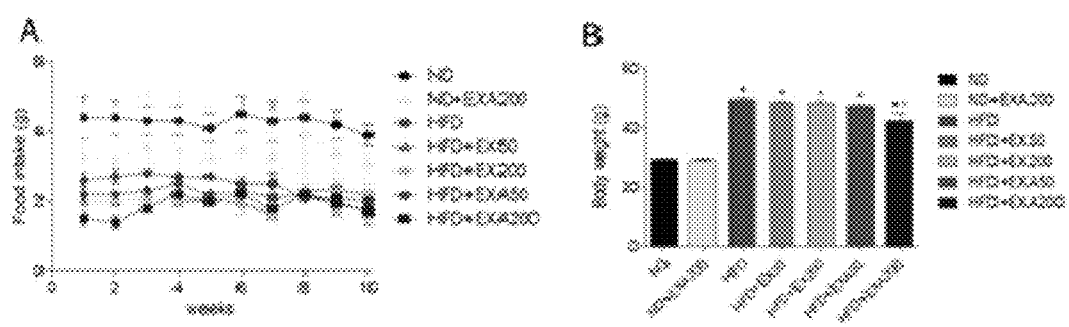
FIG. 12 in graphs A and B shows the effects of appetite reduction and weight reduction, respectively, depending on the concentration of administered exendin-4-ABD-aFaff and exendin-4.

As a result, it can be seen from FIG. 12 that the feed intake was high in the normal-diet animal experimental group, but feed intake was decreased in the high-fat-diet animal experimental group due to the high fat content of the feed. However, the high-fat diet had a high calorie (60% kcal) due to the fat content, so the body weight increased in spite of the decreased feed intake. On the other hand, unlike other comparative experimental groups, the high-fat-diet mice administered with Exendin-4-ABD-aFaff (200 nmol/kg; 6.4 mg/kg) exhibited an effect of appetite reduction for about 7 weeks and a remarkable weight-loss effect after 10 weeks.

Meanwhile, each mouse was anesthetized, whole blood was collected from the left ventricle thereof with a 1 ml syringe, and then serum and blood cells were separated using a centrifuge and sent to Green Cross Co., Ltd. for analysis of serum total cholesterol concentration.

Figure 13:
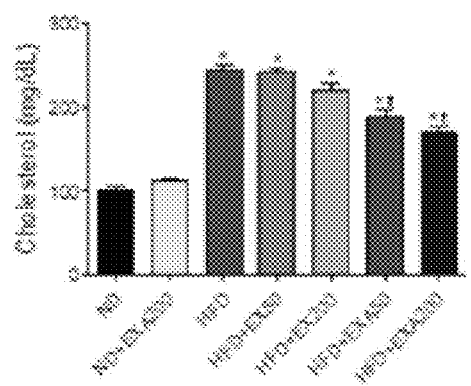
FIG. 13 shows the change in total blood cholesterol depending on the concentration of administered exendin-4-ABD-aFaff and exendin-4.

As a result, it can be seen from FIG. 13 that the serum total cholesterol concentration was increased by about 2.5 times in the high-fat-diet mice compared to the normal-diet mice, but remarkably decreased in a dose-dependent manner in the high-fat-diet mice administered with Exendin-4-ABD-aFaff. The high-fat-diet mice administered with Exendin-4 exhibited no statistically significant reduction.

5-2. Intestinal Mesenteric Fat Weight Reduction

Whole blood was collected from the left ventricle, and liver, epididymal fat, peri-renal fat, and intestinal mesenteric fat were weighed.

Figure 14:
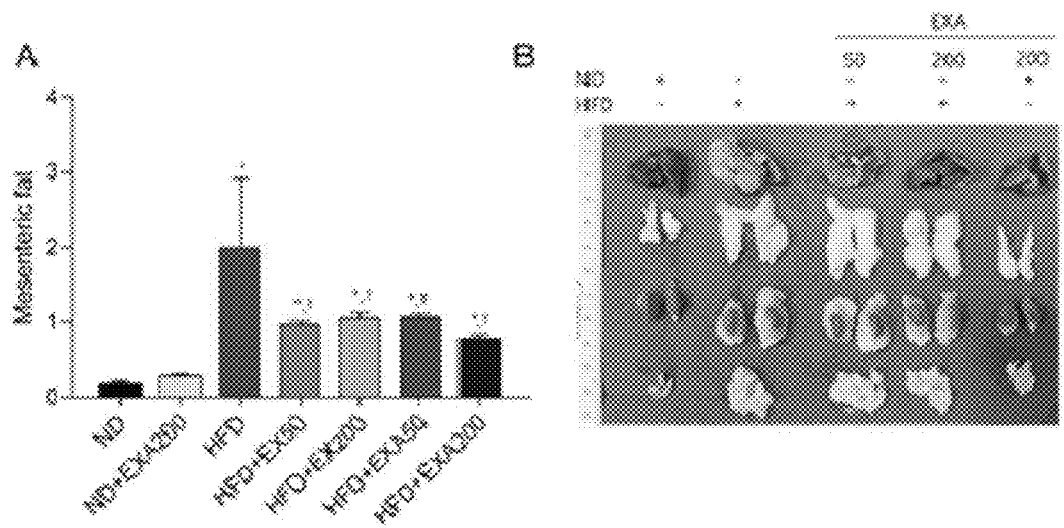
FIG. 14 shows abdominal intestinal mesenteric fat (visceral fat) depending on the concentration of administered exendin-4-ABD-aFaff and exendin-4.

As a result, it can be seen from FIG. 14 that the intestinal mesenteric fat weight of the high-fat-diet mice was increased by about 2 times compared to that of the normal-diet mice, but the high-fat-diet mice administered with Exendin-4-ABD-aFaff or Exendin-4 exhibited decreased intestinal mesenteric fat weight. In particular, high-fat-diet mice administered with Exendin-4-ABD-aFaff (200 nmol/kg; 6.4 mg/kg) were found to exhibit effective reductions in epididymal fat, peri-renal fat, and mesenteric fat.

Example 6. Effect of Long-Acting Exendin-4 (Exendin-4-ABD-aFaff) on Improvement of Cognitive Ability In order to determine the effect of administration of exendin-4-ABD-aFaff on improvement of cognitive ability, an experiment was conducted on the animal experimental group of Example 3-4.

For the long-term memory verification, the Morris water maze test was conducted. A water maze pool having a diameter of 100 cm was filled with water (21±2° C.) to a depth of 1 cm higher than a circular escape platform so that the platform was hidden, and Prima (Dongseo Foods Co., Ltd.) was released into the pool so that the platform was completely hidden. The pool was divided into four equal quadrants, that is, northeast (NE), northwest (NW), southeast (SE), and southwest (SW), among which the platform was placed in the center of the southeast (SE) quadrant, and the mouse was placed in the water such that it faced the wall at the edge of each quadrant. The mice were placed into the pool 4 times for 90 seconds per day for 4 days, and the time until the mouse climbed onto the platform (escape latency) was measured. At this time, mice that failed to climb onto the platform within 90 seconds were placed back onto the platform and allowed to remain thereon for 20 seconds. After removing the platform for the probe test on the $5^{th}$ day, that is, the last day, the mice were allowed to swim for 60 seconds, and the time for which the mouse stayed on the platform quadrant (time spent on the target platform quadrant) and the frequency of passing the platform (the number of the platform crossings) were measured. All mouse behaviors in the water maze were recorded using a video tracking system (Noldus EthoVision XT7, Noldus Information Technology, The Netherlands).

Figure 15:
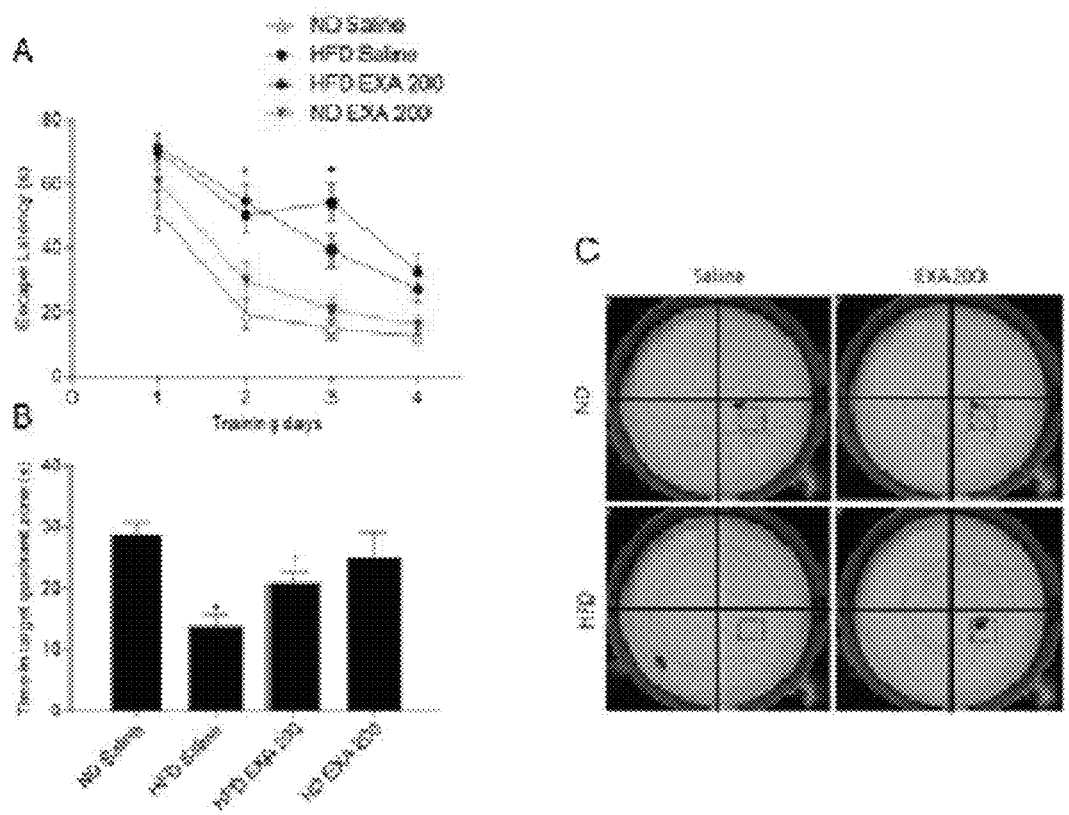
FIG. 15 shows the result of a Morris water maze test, verifying the effect of administration of exendin-4-ABD-aFaff on improvement of cognitive ability.

As a result, it can be seen from FIG. 15 that the normal diet (ND) mice exhibited a superior learning effect from day 1 to day 4 compared to the high-fat diet (HFD) mice, and the learning effect of the high-fat-diet mice treated with Exendin-4-ABD-aFaff was gradually improved (graph A). On the last day, the platform was removed, and how long each mouse stayed in the place from which it had escaped was determined. As a result, it was observed that the high-fat-diet mice (HFD) stayed on the platform for a much shorter time than the normal-diet mice, but the high-fat-diet mice administered with Exendin-4-ABD-aFaff (EXA200) had an increased residence time in the quadrant where the platform was placed (graph B). Meanwhile, the result of video camera tracking to monitor how each mouse finds the platform showed that the tracking line of the high-fat-diet mice administered with Exendin-4-ABD-aFaff (EXA200) was observed more in the quadrant where the platform was placed than the high-fat-diet mice not administered therewith (image C).

Example 7. Pharmacokinetic Evaluation of Long-Acting Exendin-4 (Exendin-4-ABD-aFaff)

Six-week-old male ICR mice were purchased from Jung-Ang Lab, Animal, Inc. and bred in the animal laboratory of Gyeongsang National University. After one week, Exendin-4 (50 nmol/kg; 0.9 mg/kg), Exendin-4-aFaff (50 nmol/kg; 1.2 mg/kg), Exendin-4-ABD (50 nmol/kg; 1.2 mg/kg) and Exendin-4-ABD-aFaff (50 nmol/kg; 1.6 mg/kg) were each administered to the ICR mice by subcutaneous injection, and then at predetermined times (0, 5 min, 10 min, 30 min, 1 h, 2 h, 4 h, 6 h, 7 h, 8 h, day 2, day 3, day 4, day 7, day 10, and day 14), plasma was collected, and the concentration in the plasma sample was assayed by size exclusion chromatography (Shodex SEC) using HPLC (Alliance 2695 HPLC of Waters).

Figure 16:
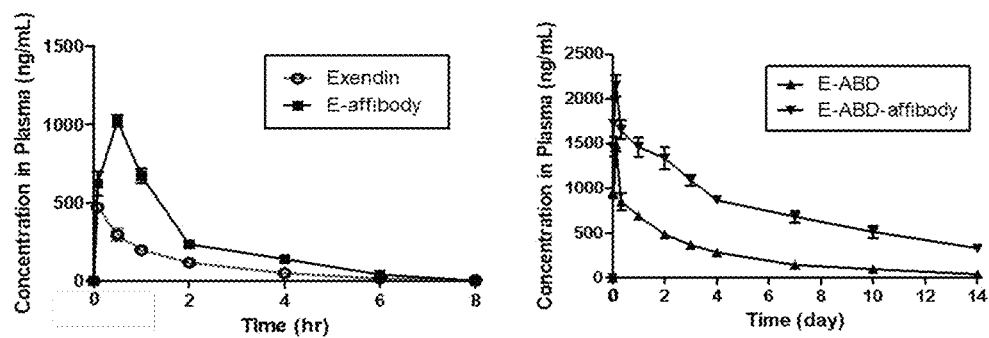
FIG. 16 shows the result of a comparison of the pharmacokinetic properties among exendin-4-ABD-aFaff (E-ABD-affibody), exendin-4 (Exendin), exendin-4-aFaff (E-affibody), and exendin-4-ABD (E-ABD).

As a result, it can be seen from FIG. 16 that Exendin-4 and Exendin-4-aFaff (E-affibody) exhibited similar plasma pharmacokinetics, and plasma half-lives of 1.46 and 1.44 hours, respectively, with no great difference therebetween. On the other hand, Exendin-4-ABD had a plasma half-life of 3.2 days, which was remarkably increased compared to Exendin-4, and Exendin-4-ABD-aFaff had a half-life of 6.4 days, which was double that of Exendin-4-ABD.

Overall, in the examples described above, the long-acting Exendin-4 (Exendin-4-ABD-aFaff) according to the present invention has a remarkably increased plasma half-life compared to the long-acting Exendin-4 such as Exendin-4-ABD, can maintain a normal blood glucose level through just by administering once every two weeks based on the stability thereof, compared to conventional long-acting formulations that should be administered at a maximum interval of once a week to maintain the normal blood glucose level. Therefore, based on the remarkable increase in residence time in the body, the long-acting Exendin-4 of the present invention is effective not only for the treatment of diabetes but also for the treatment of various complications of diabetes.

Although specific configurations of the present invention have been described in detail, those skilled in the art will appreciate that this description is provided to set forth preferred embodiments for illustrative purposes and should not be construed as limiting the scope of the present invention. Therefore, the substantial scope of the present invention is defined by the accompanying claims and equivalents thereto.

Industrial Applicability

The long-acting exendin-4 according to the present invention has a remarkably increased in-vivo half-life compared to exendin-4, which was used as a conventional therapeutic agent for diabetes, and as a result, the long-acting exendin-4 is effective not only as a therapeutic agent for diabetes, in accordance with the conventional use of exendin-4, but also in the treatment of other metabolic diseases such as obesity and fatty liver and diabetes complications, and also has the effect of alleviating cognitive impairment caused by metabolic diseases. Therefore, the long-acting exendin-4 is useful for the treatment, alleviation and prevention of patients with diabetes, other metabolic diseases, and cognitive impairment.

[Sequence Listing Free Text]

An electronic file is attached.

The invention claimed is:

1. A long-acting exendin-4, wherein an albumin-binding domain (ABD) and an anti-FcRn affibody are fused to exendin-4, wherein the exendin-4 is encoded by the nucleic acid sequence of SEQ ID NO: 4, the albumin-binding domain is encoded by the nucleic acid sequence of SEQ ID NO: 5, and the anti-FcRn affibody is encoded by the nucleic acid sequence of SEQ ID NO: 6.

2. The long-acting exendin-4 according to claim 1, wherein the exendin-4 and the albumin-binding domain are linked through a peptide linker, and the albumin-binding domain and the anti-FcRn affibody are linked through a peptide linker.

3. The long-acting exendin-4 according to claim 2, wherein the peptide linker is represented by an amino acid sequence of (GGGGS)$_4$ SEQ ID NO: 10.

4. A method for treating a metabolic disease comprising administering the long-acting exendin-4 according to claim 1 to a subject in need thereof.

5. The method according to claim 4, wherein the metabolic disease comprises at least one disease selected from the group consisting of diabetes, fatty liver, and obesity.

6. A method for treating cognitive impairment comprising administering the long-acting exendin-4 according to claim 1 to a subject in need thereof.

* * * * *

UNITED STATES PATENT AND TRADEMARK OFFICE
CERTIFICATE OF CORRECTION

| | | |
|---|---|---|
| PATENT NO. | : 12,157,761 B2 | Page 1 of 1 |
| APPLICATION NO. | : 17/299274 | |
| DATED | : December 3, 2024 | |
| INVENTOR(S) | : Gu Seob Roh et al. | |

It is certified that error appears in the above-identified patent and that said Letters Patent is hereby corrected as shown below:

In the Specification

Column 3, Line 55, "graphs A and 8B" should be -- graphs A and B --.

Column 11, Line 26, "pRA" should be -- pRλ --.

Column 13, Line 14, "DH5a" should be -- DH5α --.

Signed and Sealed this
Thirtieth Day of September, 2025

John A. Squires
*Director of the United States Patent and Trademark Office*

SEQUENCE LISTING

<160> NUMBER OF SEQ ID NOS: 10

<210> SEQ ID NO 1
<211> LENGTH: 39
<212> TYPE: PRT
<213> ORGANISM: Artificial Sequence
<220> FEATURE:
<223> OTHER INFORMATION: Exendin-4

<400> SEQUENCE: 1

His Gly Glu Gly Thr Phe Thr Ser Asp Leu Ser Lys Gln Met Glu Glu
1               5                   10                  15

Glu Ala Val Arg Leu Phe Ile Glu Trp Leu Lys Asn Gly Gly Pro Ser
            20                  25                  30

Ser Gly Ala Pro Pro Pro Ser
        35

<210> SEQ ID NO 2
<211> LENGTH: 45
<212> TYPE: PRT
<213> ORGANISM: Artificial Sequence
<220> FEATURE:
<223> OTHER INFORMATION: Albumin Binding Domain

<400> SEQUENCE: 2

Leu Lys Glu Ala Lys Glu Lys Ala Ile Glu Glu Leu Lys Lys Ala Gly
1               5                   10                  15

Ile Thr Ser Asp Tyr Tyr Phe Asp Leu Ile Asn Lys Ala Lys Thr Val
            20                  25                  30

Glu Gly Val Asn Ala Leu Lys Asp Glu Ile Leu Lys Ala
        35                  40                  45

<210> SEQ ID NO 3
<211> LENGTH: 58
<212> TYPE: PRT
<213> ORGANISM: Artificial Sequence
<220> FEATURE:
<223> OTHER INFORMATION: Anti-FcRn affibody

<400> SEQUENCE: 3

Val Asp Ala Lys Tyr Ala Lys Glu Phe Glu Ser Ala Ala His Glu Ile
1               5                   10                  15

Arg Trp Leu Pro Asn Leu Thr Tyr Asp Gln Arg Val Ala Phe Ile His
            20                  25                  30

Lys Leu Ser Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 4
<211> LENGTH: 117
<212> TYPE: DNA
<213> ORGANISM: Artificial Sequence
<220> FEATURE:
<223> OTHER INFORMATION: Exendin-4

<400> SEQUENCE: 4
cacggcgagg gcacctttac cagcgacctg agcaagcaaa tggaagagga agcggttcgt     60
ctgtttattg agtggctgaa aaatggcggt ccgagcagcg gtgctccgcc gccgagc      117

<210> SEQ ID NO 5
<211> LENGTH: 135
<212> TYPE: DNA
<213> ORGANISM: Artificial Sequence
<220> FEATURE:
<223> OTHER INFORMATION: Albumin Binding Domain

<400> SEQUENCE: 5
ctgaaagagg cgaaggaaaa agcgatcgag gaactgaaga aagcgggtat taccagcgac     60
tactatttcg atctgatcaa caaggcgaaa accgtggagg gtgttaacgc gctgaaggac    120

-continued

```
gaaattctga aagcg                                                    135

<210> SEQ ID NO 6
<211> LENGTH: 174
<212> TYPE: DNA
<213> ORGANISM: Artificial Sequence
<220> FEATURE:
<223> OTHER INFORMATION: Anti-FcRn Affibody

<400> SEQUENCE: 6
gtggatgcga agtatgcgaa agagttcgaa agcgcggcgc atgagatccg ttggctgccg    60
aacctgacct atgatcagcg tgttgcgttt attcacaaac tgagcgacga tccgagccag   120
agcagcgaac tgctgagcga agcgaaaaaa ctgaacgata gccaagcgcc gaag         174

<210> SEQ ID NO 7
<211> LENGTH: 46
<212> TYPE: PRT
<213> ORGANISM: Artificial Sequence
<220> FEATURE:
<223> OTHER INFORMATION: ABD 035

<400> SEQUENCE: 7

Leu Ala Glu Ala Lys Val Leu Ala Asn Arg Glu Leu Asp Lys Tyr Gly
1               5                   10                  15

Val Ser Asp Phe Tyr Lys Arg Leu Ile Asn Lys Ala Lys Thr Val Glu
            20                  25                  30

Gly Val Glu Ala Leu Lys Leu His Ile Leu Ala Ala Leu Pro
        35                  40                  45

<210> SEQ ID NO 8
<211> LENGTH: 58
<212> TYPE: PRT
<213> ORGANISM: Artificial Sequence
<220> FEATURE:
<223> OTHER INFORMATION: Anti-FcRn affibody

<400> SEQUENCE: 8

Val Asp Ala Lys Tyr Ala Lys Glu Gln Asp Ala Ala Ala His Glu Ile
1               5                   10                  15

Arg Trp Leu Pro Asn Leu Thr Phe Asp Gln Arg Val Ala Phe Ile His
            20                  25                  30

Lys Leu Ala Asp Asp Pro Ser Gln Ser Ser Glu Leu Leu Ser Glu Ala
        35                  40                  45

Lys Lys Leu Asn Asp Ser Gln Ala Pro Lys
    50                  55

<210> SEQ ID NO 9
<211> LENGTH: 58
<212> TYPE: PRT
<213> ORGANISM: Artificial Sequence
<220> FEATURE:
<223> OTHER INFORMATION: Anti-FcRn affibody

<400> SEQUENCE: 9

Val Asp Ala Lys Tyr Ala Lys Glu Trp Met Arg Ala Ala His Glu Ile
1               5                   10                  15

Arg Trp Leu Pro Asn Leu Thr Phe Asp Gln Arg Val Ala Phe Ile His
            20                  25                  30

Lys Leu Glu Asp Asp Pro Ser Gln Ser Ser Glu Leu Leu Ser Glu Ala
        35                  40                  45
```

```
Lys Lys Leu Asn Asp Ser Gln Ala Pro Lys
    50                  55

<210> SEQ ID NO 10
<211> LENGTH: 20
<212> TYPE: PRT
<213> ORGANISM: Artificial Sequence
<220> FEATURE:
<223> OTHER INFORMATION: peptide linker

<400> SEQUENCE: 10

Gly Gly Gly Gly Ser Gly Gly Gly Ser Gly Gly Gly Gly Ser Gly
1               5                   10                  15

Gly Gly Gly Ser
            20
```